(12) United States Patent
Chen

(10) Patent No.: US 9,113,997 B2
(45) Date of Patent: Aug. 25, 2015

(54) ANKLE PROTECTING DEVICE

(76) Inventor: Tsan-Jee Chen, Taipei (TW)

( * ) Notice: Subject to any disclaimer, the term of this patent is extended or adjusted under 35 U.S.C. 154(b) by 157 days.

(21) Appl. No.: 13/526,699

(22) Filed: Jun. 19, 2012

(65) Prior Publication Data

US 2013/0338558 A1    Dec. 19, 2013

(51) Int. Cl.
 *A61F 5/00* (2006.01)
 *A61F 5/01* (2006.01)

(52) U.S. Cl.
 CPC ....... *A61F 5/0111* (2013.01); *A61F 2005/0165* (2013.01)

(58) Field of Classification Search
 CPC ............ A43B 7/20; A43B 5/00; A43B 13/12; A43B 13/141; A43B 13/16; A61F 5/0111; A61F 2/66; A61F 2002/5003; A61F 2002/6621; A61F 2002/6642; A61F 5/0127; A61F 2002/30434; A61F 2002/30438; A61F 2002/5009; A61F 2002/503; A61F 2005/0165; A61F 5/04; A63C 10/045; A63C 10/04; A63C 10/18; A63C 10/24; A63C 10/285; B63B 35/812; B63B 35/7936

USPC ............ 128/869, 882, 892–894; 602/16–28, 602/60–62, 65, 66, 5

See application file for complete search history.

(56) References Cited

U.S. PATENT DOCUMENTS

| | | | |
|---|---|---|---|
| 7,128,725 B2 * | 10/2006 | Rabe | 602/27 |
| 7,828,758 B2 * | 11/2010 | Clements et al. | 602/23 |
| 8,007,454 B1 * | 8/2011 | Zerr et al. | 602/23 |
| 2005/0145256 A1 * | 7/2005 | Howard et al. | 128/882 |
| 2007/0213649 A1 * | 9/2007 | Gaylord et al. | 602/27 |

* cited by examiner

*Primary Examiner* — Michael Brown
(74) *Attorney, Agent, or Firm* — Ming Chow; Sinorica, LLC

(57) ABSTRACT

An ankle protecting device comprises: a wrapping sheath having a lower-leg sheath, a foot sheath and a loincloth that are integrated with thereof, the loincloth constricts the wrapping sheath on a sole, an ankle and a lower leg and is adjustable for tightness thereof; an internal supporting plate and an outer supporting plate fastened on the left and right sides of the wrapping sheath respectively, the shapes of the internal supporting plate and the outer supporting plate are symmetrical to each other, the internal supporting plate and the outer supporting plate 50b elongate to be over the ankle along the internal and outer sides of the lower leg and then to the two sides of the sole toward the top of the sole; and a foot bottom supporting plate fastened on the bottom of the foot sheath.

7 Claims, 5 Drawing Sheets

ANKLE PROTECTING DEVICE

BACKGROUND OF THE INVENTION

1. Field of the Invention

The present invention is a human body protecting device, more particularly to an ankle protecting device that provides adequate supports and increases the stability of an ankle.

2. Description of the Prior Art

Adequate sports are good to health of human beings, but sports injuries happen as always, and ankle sprain is the highest possibility for sports injuries.

The factors to ankle sprain are mostly as that a body is loosing balance and is stepping on other people's feet or is being tumbled while landing. Local joint swelling, pain, and even causing a fracture are happening while in ankle sprain. After happening, if the treatment is not adequate, tibia, talus within the ankle joint (also known as ankle) and calcaneal may be displaced or stiff tight. Hence, ankle may be in trouble very easily while moving, since the joint is not active enough and easily looses balance thereof.

Prior ankle protecting devices are plentiful, and the most common one is an elastic bandage, wherein a tubular elastic bandage is capable of constricting the ankle, and another stripe bandage can wind around the ankle so as to prevent ankle injuries. Such bandages are easy to construct and provide basic protections and preventions due to the retractility and elasticity for support and oppression. Further that, the winding ways of some elastic bandages are more complex and inconvenient, not suitable for general users.

Another prior ankle protecting device includes a tubular elastic sheath and an elastic piece that are on a lower leg or heel and on the left and right sides of the elastic sheath for constricting an ankle. The angles of internal flipping and outer flipping of the ankle are restricted by the elastic sheath and the elastic piece in order to reduce the possibility of injury. Such ankle protecting device uses the two elastic pieces elongating downward to be over the ankle and the tubular elastic sheath to provide supporting forces. Such elastic piece and sheath are better than aforesaid but only restrict the internal flipping and outer flipping and do not provide suitable restriction and protection for the forward flipping and backward flipping of the sole.

SUMMARY OF THE INVENTION

The main objective of the present invention is to provide an ankle protecting device that restricts the angles of inner flipping, outer flipping, forward flipping, and backward flipping of the sole, so that the stability of the ankle is increased, the possibility of sprain is decreased, further, the effectiveness of oppression and preventing swelling are achieved as well.

An embodiment of the ankle protecting device of the present invention comprises:
a wrapping sheath, which has retractility and elasticity and has a lower-leg sheath, a foot sheath and at least one loincloth that are integrated with thereof, the loincloth constricts the wrapping sheath on a sole, an ankle and a lower leg and is adjustable for tightness thereof;
an internal supporting plate and an outer supporting plate, which are fastened on the left and right sides of the wrapping sheath respectively, the shapes of the internal supporting plate and the outer supporting plate are symmetrical to each other, the internal supporting plate and the outer supporting plate elongate to be over the ankle along the internal and outer sides of the lower leg and then to the two sides of the sole toward the top of the sole; and
a foot bottom supporting plate, which is fastened on the bottom of the foot sheath, a three-point support is formed by the foot bottom supporting plate, the internal supporting plate and the outer supporting plate in order to support the internal and outer sides of the lower leg, the ankle and the sole, and the angles of inner flipping, outer flipping, forward flipping, and backward flipping of the sole shall be restricted, so that the stability of the ankle is increased, the possibility of sprain is decreased, further, the effectiveness of oppression and preventing swelling are achieved as well.

For a preferred embodiment, both the lower-leg sheath and the foot sheath have three surfaces, the lower-leg sheath has a back surface, a left side surface and a right side surface in order to wrap around the back side, the inner side and the outer side of the lower leg, the foot sheath of the wrapping sheath has a bottom portion, a left side portion and a right side portion in order to wrapped around the bottom portion, the inner side and the outer side of the sole.

For a preferred embodiment, the foot sheath has a bottom portion, a left side portion, a right side portion, and a top surface portion connecting the left side portion and the right side portion in order to wrapped around the bottom portion, the back portion, the inner side and the outer side of the sole.

For a preferred embodiment, the internal supporting plate, the outer supporting plate and the foot bottom supporting plate are made by aluminum or plastic.

According to above descriptions, the ankle protecting device is able to constrict the wrapping sheath on the sole, the ankle and the lower leg via the loincloth and is adjustable for tightness thereof. A three-point support is formed by the foot bottom supporting plate, the internal supporting plate and the outer supporting plate in order to support the internal and outer sides of the lower leg, the ankle and the sole, and the angles of inner flipping, outer flipping, forward flipping, and backward flipping of the sole shall be restricted, so that the stability of the ankle is increased, the possibility of sprain is decreased, further, the effectiveness of oppression and preventing swelling are achieved as well.

Other and further features, advantages, and benefits of the invention will become apparent in the following description taken in conjunction with the following drawings. It is to be understood that the foregoing general description and following detailed description are exemplary and explanatory but are not to be restrictive of the invention. The accompanying drawings are incorporated in and constitute a part of this application and, together with the description, serve to explain the principles of the invention in general terms. Like numerals refer to like parts throughout the disclosure.

BRIEF DESCRIPTION OF THE DRAWINGS

The objects, spirits, and advantages of the preferred embodiments of the present invention will be readily understood by the accompanying drawings and detailed descriptions, wherein.

DETAILED DESCRIPTION OF THE INVENTION

Following preferred embodiments and figures will be described in detail so as to achieve aforesaid objects.

Figure 1:
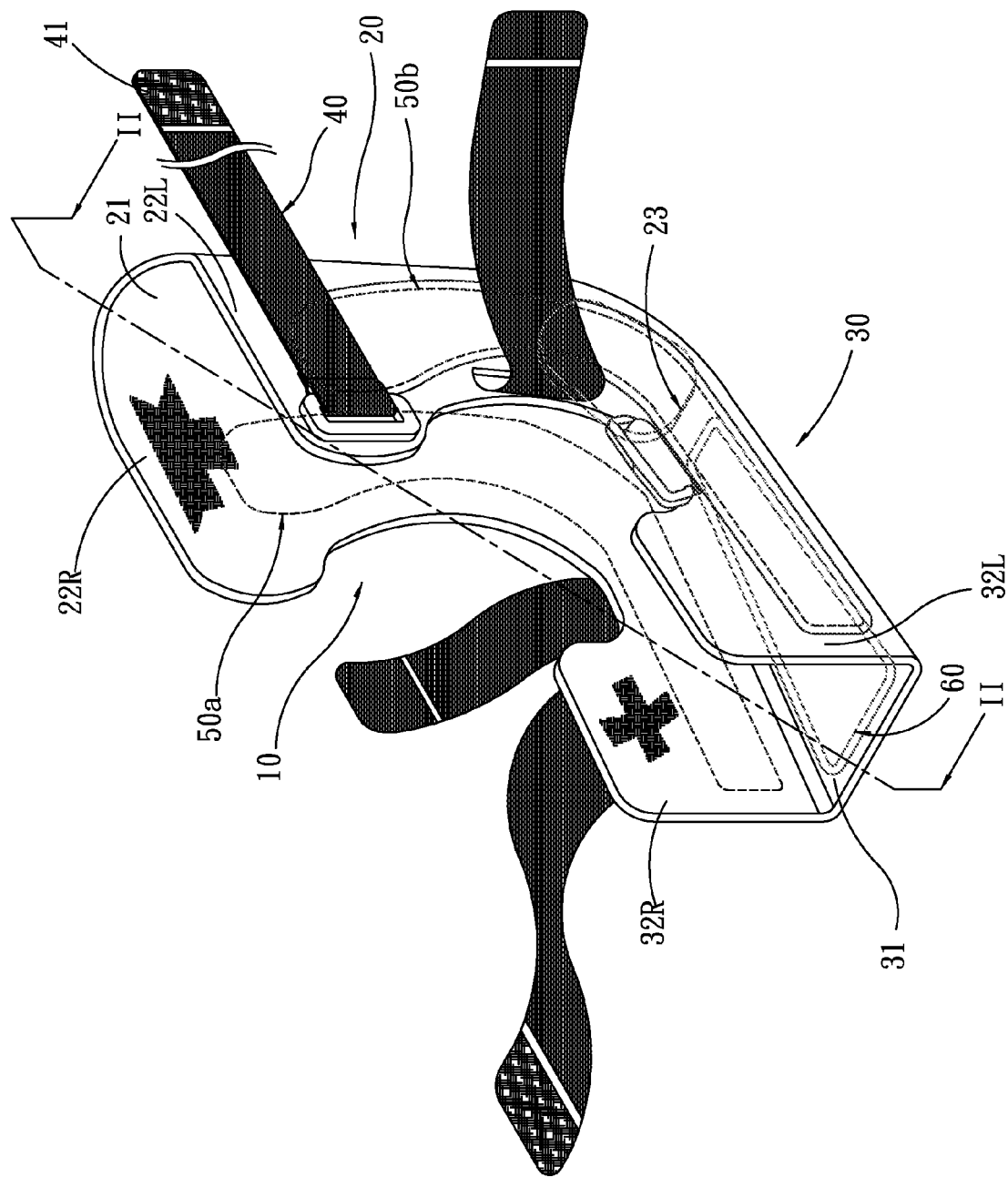
FIG. 1 illustrates a schematic 3-D view of a first preferred embodiment of the ankle protecting device of the present invention.
Figure 3:
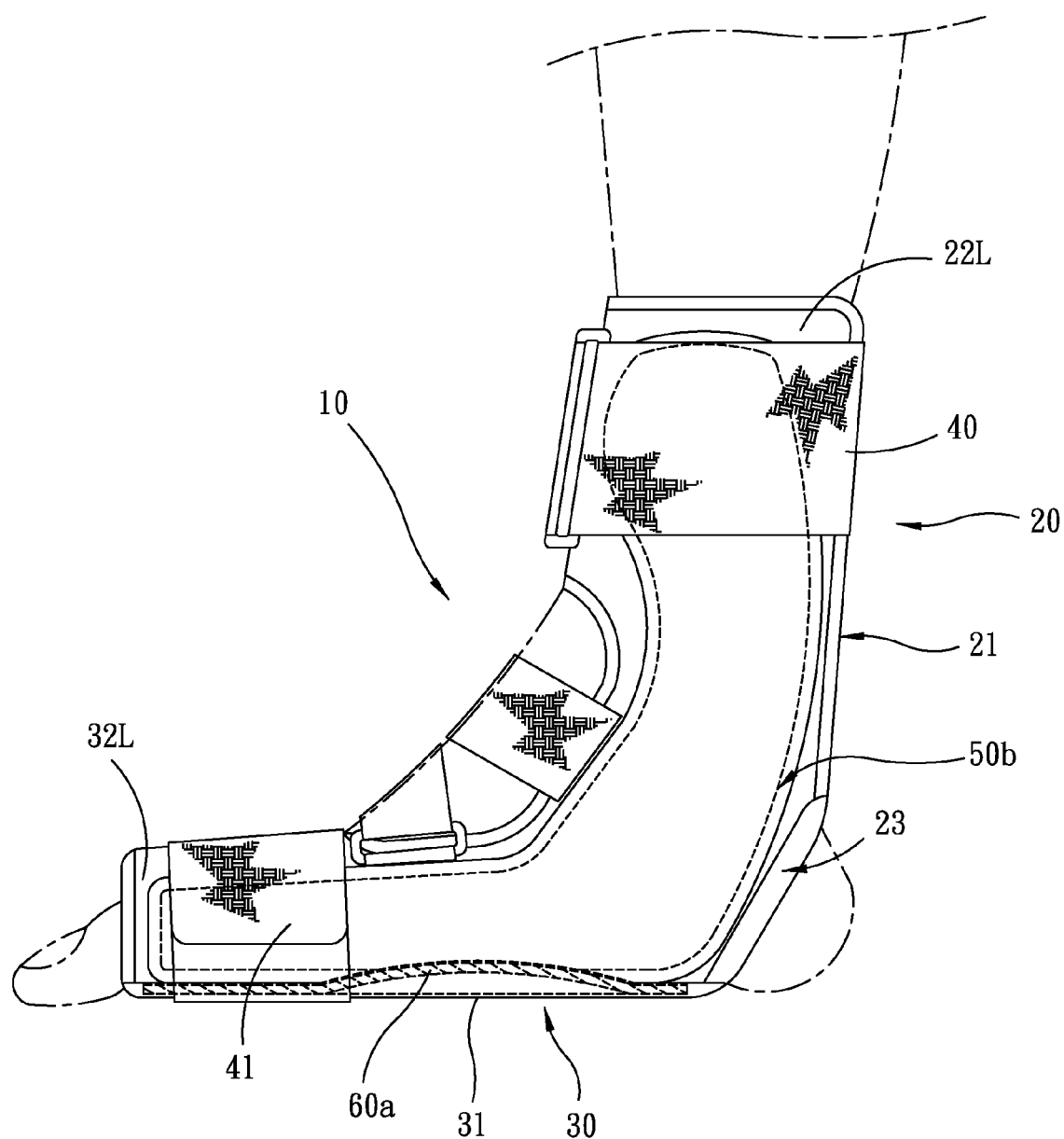
FIG. 3 illustrates an application view of the ankle protecting device.

With reference to FIG. 1, which illustrates a schematic 3-D view of a first preferred embodiment of the ankle protecting device of the present invention. The ankle protecting device includes:

a wrapping sheath 10, which has a lower-leg sheath 20, a foot sheath 30 and a loincloth 40 that are integrated with thereof, the loincloth 40 constricts the wrapping sheath 10 on a sole, an ankle and a partial lower leg above the ankle and is adjustable for tightness thereof (referring to FIG. 3 as well);

an internal supporting plate 50*a* and an outer supporting plate 50*b*, which are fastened on the left and right sides of the wrapping sheath 10 respectively, the shapes of the internal supporting plate 50*a* and the outer supporting plate 50*b* are symmetrical to each other, the internal supporting plate 50*a* and the outer supporting plate 50*b* elongate downward to be over the ankle along the internal and outer sides of the lower leg and then to the two sides of the sole toward the top of the sole; and a foot bottom supporting plate 60, which are fastened on the bottom 31 of the foot sheath 30.

A type of the wrapping sheath 10 in the first preferred embodiment is as shown in FIG. 1, both the lower-leg sheath 20 and the foot sheath 30 have three surfaces, the lower-leg sheath 20 has a back surface 21, a left side surface 22L and a right side surface 22R in order to wrap around the back side, the inner side and the outer side of the lower leg, the foot sheath 30 of the wrapping sheath 10 has a bottom portion 31, a left side portion 32L and a right side portion 32R in order to wrapped around the bottom portion, the inner side and the outer side of the sole, the connecting position of the back surface 21 of the lower-leg sheath 20 and the bottom portion 31 of the foot sheath 30 has a heel positioning hole 23 so as to expose the heel of a user.

The number of the loincloth 40 can be plural, and the loincloth 40 of the preferred embodiment is a flat ribbon fabric with a Velcro 41 thereon and winds around the peripheries of the lower-leg sheath 20 and the foot sheath 30. While the user wears the wrapping sheath 10 on the lower leg and the sole, the loincloths 40 are able to constrict the wrapping sheath 10 on the sole, the ankle and the partial lower leg above the ankle and adjust the tightness thereof according to the Velcros 41. Hence, a three-point support is formed by the foot bottom supporting plate 60, the internal supporting plate 50*a* and the outer supporting plate 50*b* in order to support the internal and outer sides of the lower leg, the ankle and the sole, and the angles of inner flipping, outer flipping, forward flipping, and backward flipping of the sole shall be restricted, so that the stability of the ankle is increased, the possibility of sprain is decreased, further, the effectiveness of oppression and preventing swelling are achieved as well (referring to FIG. 3).

Another type of the loincloth 40 is a flat ribbon fabric with plural buttons and button holes thereon and winds around the peripheries of the lower-leg sheath 20 and the foot sheath 30. The tightness of the loincloth 40 is adjustable through the fastening positions of the buttons and button holes. A third type of the loincloth 40 is a flat ribbon fabric with plural male/female buckles thereon and winds around the peripheries of the lower-leg sheath 20 and the foot sheath 30. The tightness of the loincloth 40 is adjustable through the fastening positions of the male buckles and female buckles.

One type of the flat ribbon fabric of the loincloth 40 is made of canvas that is not retractable but tough. By means of the fastening positions of the Velcros 41, the buttons and button holes and the male/female buckles, the tightness of the loincloth 40 is variable.

Another type of the flat ribbon fabric of the loincloth 40 is made of bandage that is retractable and elastic. By means of the fastening positions of the Velcros 41, the buttons and button holes and the male/female buckles, the tightness of the loincloth 40 is changeable.

Figure 2:
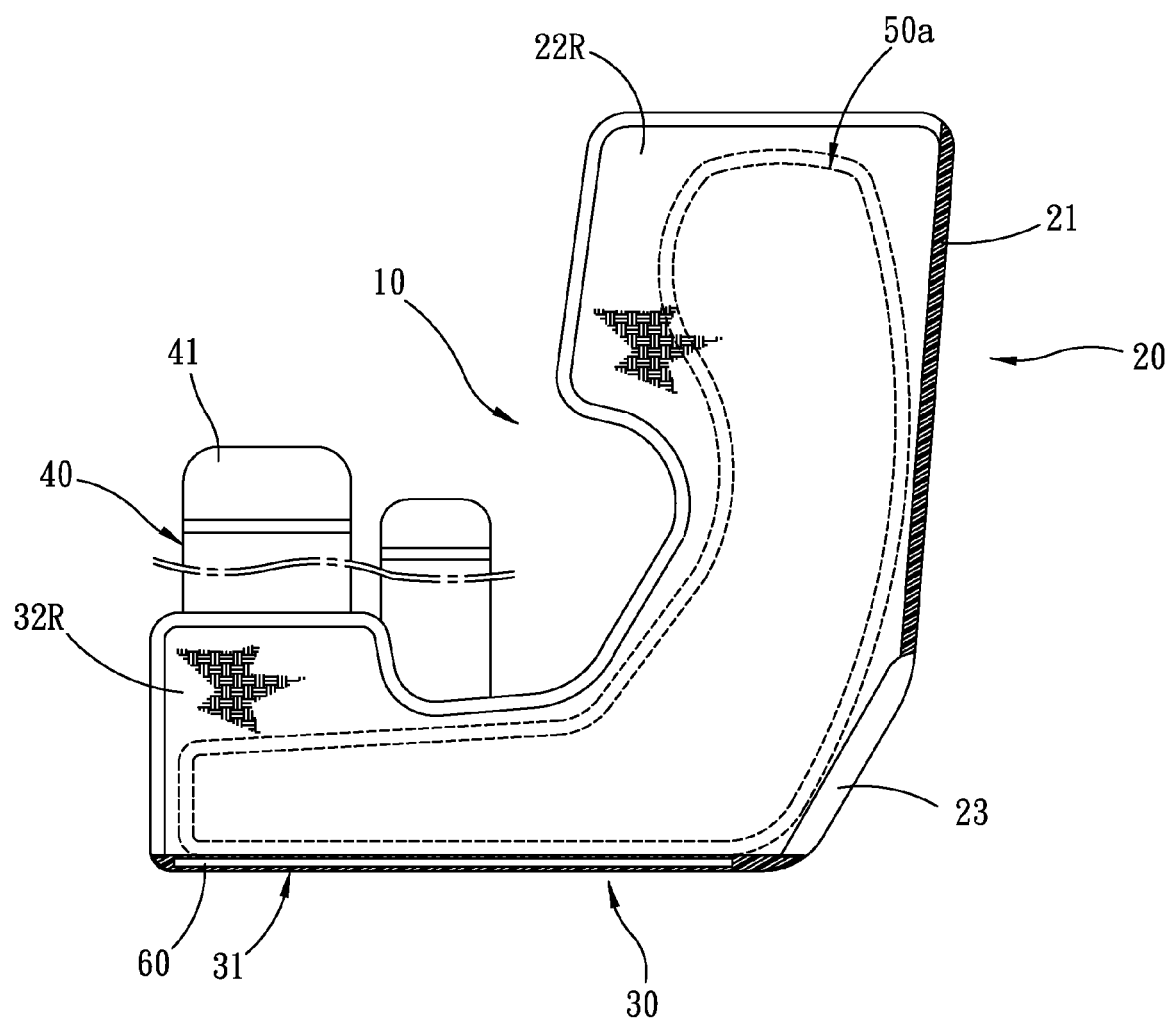
FIG. 2 illustrates a schematic side view of a line II-II in FIG. 1 and shows the side shape of a foot bottom supporting plate.

Another type of the wrapping sheath 10 is made of elastic fabric and cloth, the left and right sides of the wrapping sheath 10 and the bottom portion 31 of the foot sheath 30 have an interlining respectively, and the applied structure is consisted of a double-layer elastic fabric or a double-layer cloth sewed together. The internal supporting plate 50*a*, the outer supporting plate 50*b* and the foot bottom supporting plate 60 are made by aluminum or plastic. The foot bottom supporting plate 60 is disposed into the interlining of the bottom portion 31 of the foot sheath 30 (referring to FIG. 2). The internal supporting plate 50*a* and the outer supporting plate 50*b* are disposed into the interlinings of the left and right sides of the wrapping sheath 10. Hence, a three-point support is formed by the foot bottom supporting plate 60, the internal supporting plate 50*a* and the outer supporting plate 50*b* in order to support the internal and outer sides of the lower leg, the ankle and the sole, and the angles of inner flipping, outer flipping, forward flipping, and backward flipping of the sole shall be restricted, so that the stability of the ankle is increased, the possibility of sprain is decreased, further, the effectiveness of oppression and preventing swelling are achieved as well.

Figure 4:
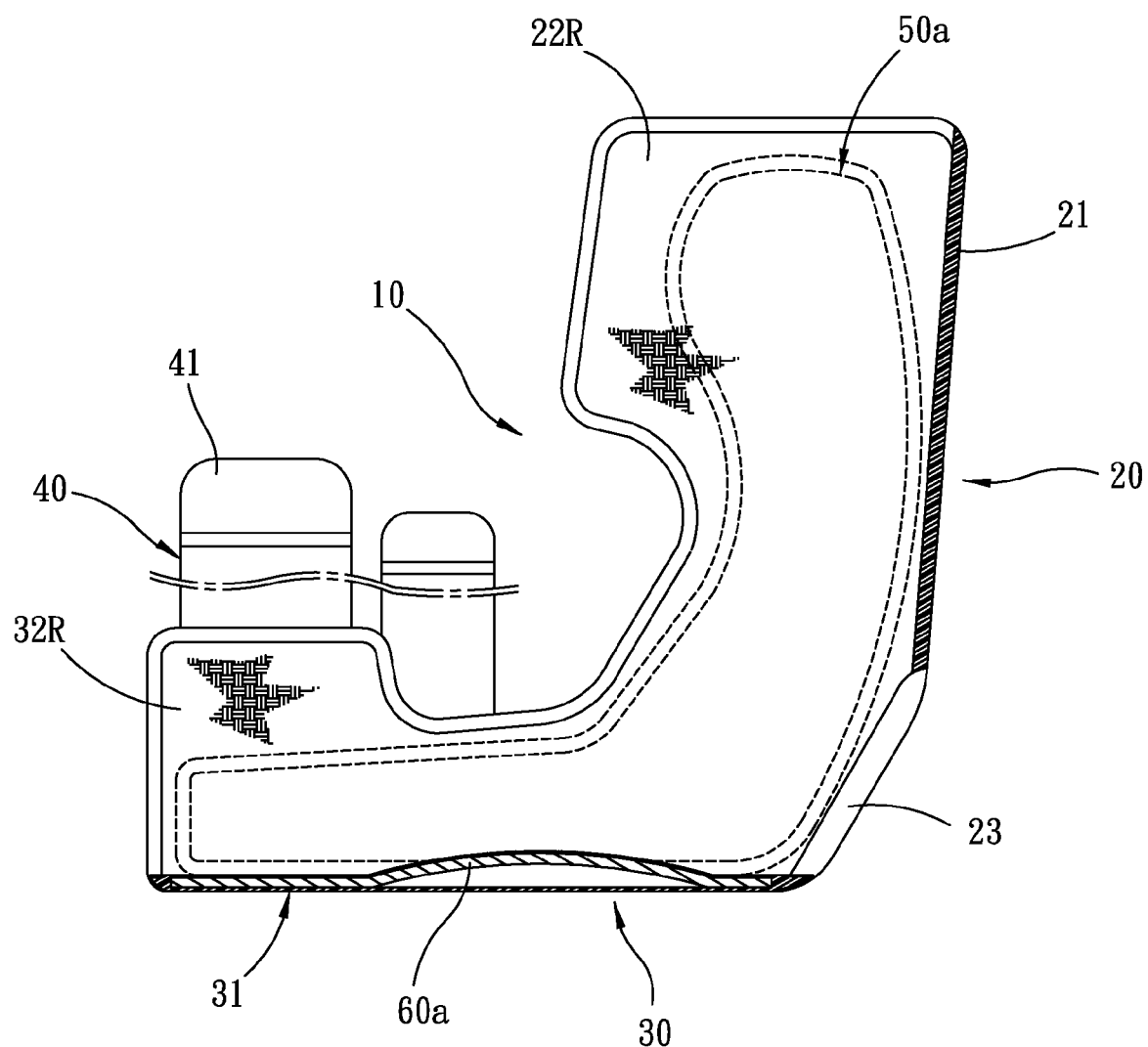
FIG. 4 illustrates another type of the foot bottom supporting plate and shows that the shape of the foot bottom supporting plate is to fit an arch.

One type of the foot bottom supporting plate 60 is a planar element with a straight surface (referring to FIG. 2); another foot bottom supporting plate 60*a* is shaped to fit the arch of the sole in order to provide the comfort of the bottom of the sole and a support with ergonomics (referring to FIG. 4).

Figure 5:
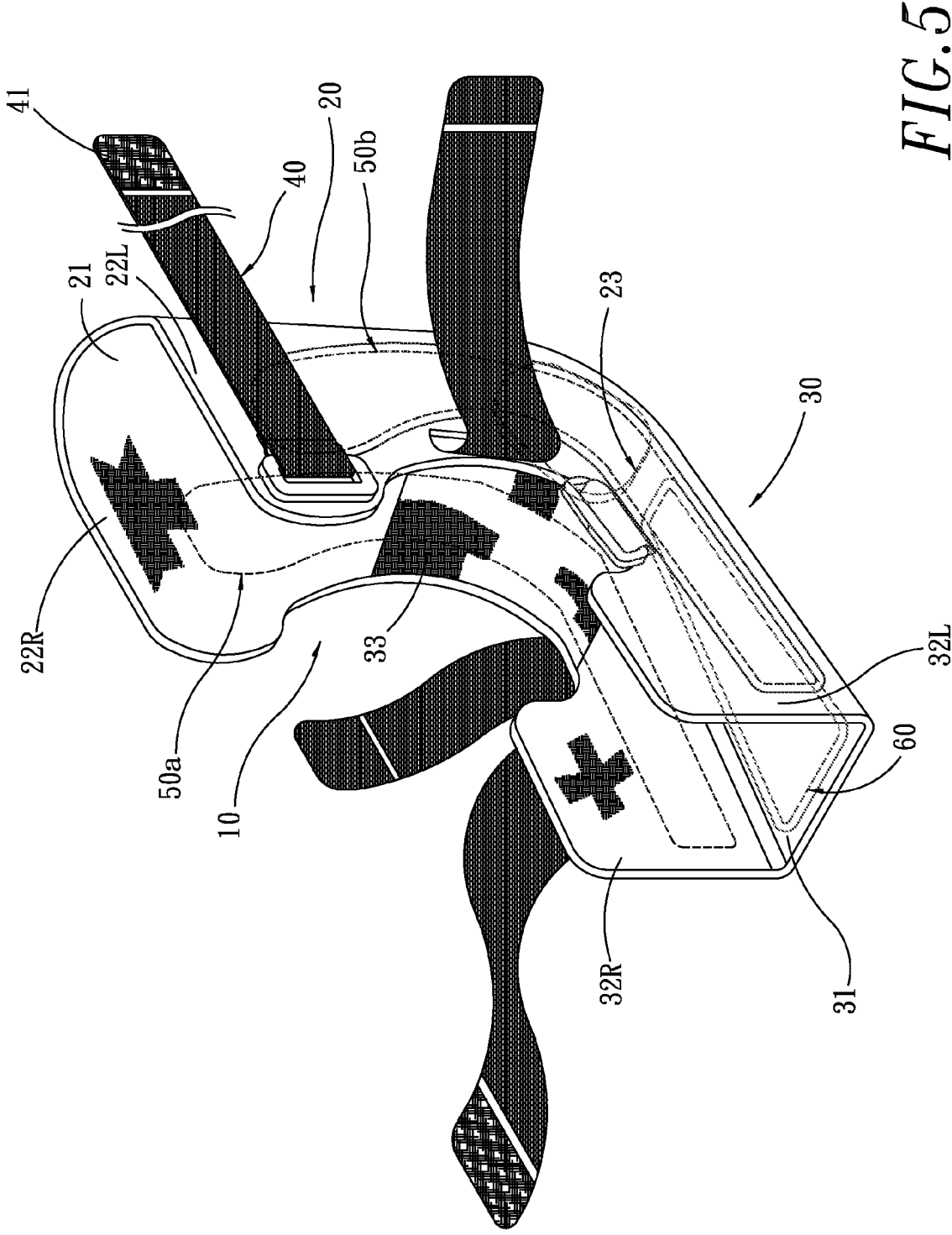
FIG. 5 illustrates a schematic 3-D view of a second preferred embodiment of the ankle protecting device of the present invention, wherein a foot sheath has a a top surface portion connecting a left side portion and a right side portion.

Another type of the wrapping sheath is as shown in FIG. 5, wherein the foot sheath 30 has a bottom portion 31, a left side portion 32L, a right side portion 32R, and a top surface portion 33 connecting the left side portion 32L and the right side portion 32R in order to wrapped around the bottom portion, the back portion, the inner side and the outer side of the sole, wherein the top surface portion 33 of the foot sheath 30 is made of an elastic fabric or a cloth, and a better feature is good permeability. Further, the top surface portion 33 of the foot sheath 30 is easily let the sole of the user be through but not loosed.

Although the invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. An ankle protecting device comprising:
a wrapping sheath having a lower-leg sheath, a foot sheath and a loincloth that are integrated with thereof, the loincloth constricting the wrapping sheath on a sole, an ankle and a lower leg and being adjustable for tightness thereof, the lower-leg sheath of the wrapping sheath has a back surface, a left side surface and a right side surface in order to wrap around the back side, the inner side and the outer side of the lower leg, the foot sheath of the wrapping sheath having a bottom portion, a left side portion and a right side portion in order to wrapped around the bottom portion, the foot sheath further comprises a top surface portion connecting the left side portion and the right side portion, the inner side and the outer side of the sole, the connecting position of the back surface of the lower-leg sheath and the bottom portion of the foot sheath having a heel positioning hole, the number of the loincloth can be plural, the loincloth being a flat ribbon fabric with a hook and loop fastener thereon and winding around the peripheries of the lower-leg sheath and the foot sheath;

an internal supporting plate and an outer supporting plate fastened on the left and right sides of the wrapping sheath respectively, the shapes of the internal supporting plate and the outer supporting plate being symmetrical to each other, the internal supporting plate and the outer supporting plate elongating to be over the ankle along the internal and outer sides of the lower leg and then to the two sides of the sole toward the top of the sole; and a foot bottom supporting plate fastened on the bottom of the foot sheath, the foot bottom supporting plate being disposed in the interlining of the bottom portion of the foot sheath, the internal supporting plate and the outer supporting plate being disposed in interlinings of left and right sides of the wrapping sheath.

2. The ankle protecting device according to claim 1, wherein the wrapping sheath is made of elastic fabric and cloth, so that the wrapping sheath has retractility and elasticity, the left and right sides of the wrapping sheath and the bottom portion of the foot sheath having an interlining respectively, the foot bottom supporting plate being disposed into the interlining of the bottom portion of the foot sheath, the internal supporting plate and the outer supporting plate being disposed into the interlinings of the left and right sides of the wrapping sheath.

3. The ankle protecting device according to claim 1, wherein the flat ribbon fabric of the loincloth is made of canvas that is not retractable but tough.

4. The ankle protecting device according to claim 1, wherein the flat ribbon fabric of the loincloth is made of bandage that is retractable and elastic.

5. The ankle protecting device according to claim 1, wherein the internal supporting plate, the outer supporting plate and the foot bottom supporting plate are made by aluminum or plastic.

6. The ankle protecting device according to claim 1, wherein the foot bottom supporting plate is a planar element with a straight surface.

7. The ankle protecting device according to claim 1, wherein the foot bottom supporting plate is shaped to fit the arch of the sole.

\* \* \* \* \*